United States Patent [19]

Klein

[11] 4,436,510
[45] Mar. 13, 1984

[54] ORTHODONTIC CHAIN APPLICATION TOOL

[75] Inventor: Paul E. Klein, Lake Oswego, Oreg.

[73] Assignee: Modcom, Inc., Canby, Oreg.

[21] Appl. No.: 411,496

[22] Filed: Aug. 25, 1982

[51] Int. Cl.³ .............................................. A61C 3/00
[52] U.S. Cl. ....................................... 433/4; 433/159; 221/310; 206/390
[58] Field of Search ................ 433/4, 3, 159; 221/26, 221/199, 310; 206/820, 390

[56] References Cited

U.S. PATENT DOCUMENTS

| | | | |
|---|---|---|---|
| 1,143,927 | 6/1915 | Allen | 433/159 |
| 3,085,339 | 4/1963 | Wolfe | 433/4 |
| 3,903,601 | 9/1975 | Anderson et al. | 433/3 |
| 4,001,940 | 1/1977 | Cusato | 433/3 |
| 4,106,374 | 8/1978 | Dragan | 433/4 |
| 4,217,686 | 8/1980 | Dragan | 433/4 |
| 4,277,236 | 7/1981 | Kurz | 433/3 |

FOREIGN PATENT DOCUMENTS

| | | | |
|---|---|---|---|
| 771517 | 11/1967 | Canada | 206/820 |
| 563745 | 6/1977 | U.S.S.R. | 221/310 |

*Primary Examiner*—John J. Wilson
*Attorney, Agent, or Firm*—Kolisch, Hartwell & Dickinson

[57] ABSTRACT

An applicator tool for dispensing and clamping individual loops in an orthodontic loop chain which is composed of a series of elastomeric loops connected by breakaway isthmuses. The tool includes a pair of loop-gripping tips adapted for clamping an end loop in the chain in a manner permitting the clamped loop to be placed on an orthodontic tooth appliance, to secure an archwire thereto. A constriction zone formed in the tool, adjacent the loop-gripping tips, functions to restrain the chain at positions where successive end loops are placed for clamping between the tool tips. The chain is advanced in the tool, in a loop-by-loop manner, by exerting a force on the chain in a downstream direction, to pull a restrained chain loop through the constriction zone by reversible loop elongation. The force required to advance the chain by one loop is less than that required to break an isthmus in the chain.

2 Claims, 5 Drawing Figures

ORTHODONTIC CHAIN APPLICATION TOOL

BACKGROUND AND SUMMARY OF THE INVENTION

The present invention relates to an orthodontic-loop applicator tool, and more particularly, to a tool for use with an orthodontic loop chain.

A common type of orthodontic apparatus employs metal bands which are mounted, as by cementing, on a person's teeth. Each band is provided with a bracket which receives an archwire that is adapted to be attached to the tooth-mounted brackets to produce tooth-positioning forces. In recent years, elastomeric loops have become a popular type of ligature for fastening an archwire to such an orthodontic bracket.

In my copending patent application, Ser. No. 344,292, filed Feb. 1, 1982, for "ORTHODONTIC ELASTOMER CHAIN WITH CONTROLLED BREAKAWAY ISTHMUSES", I disclose an orthodontic loop chain for facilitating dispensing and attaching orthodontic loops individually to orthodontic tooth appliances. The chain is composed of a series of elastomeric loops connected by breakaway isthmuses which allow chain loops to be detached as individuals by a sharp pulling force which breaks an isthmus.

The present invention contemplates a tool which is especially adapted for use in dispensing and clamping the loops in such a chain in a loop-by-loop manner to permit their placement as individuals on different ligating brackets.

Accordingly, a general object of the present invention is to provide an applicator tool for use in dispensing and clamping the loops in such a chain in a manner which allows the loops to be installed readily and conveniently, loop-by-loop.

Another object of the invention is to provide such a tool which is manipulatable both to fasten the loops in such a chain to a tooth bracket, and to advance the chain, loop-by-loop, in an indexed manner.

The tool of the present invention is intended for use with an orthodontic loop chain composed of a series of elastomeric loops linearly connected by breakaway isthmuses. The tool includes a pair of loop-gripping tips adapted for clamping an end loop in the chain in a manner permitting the clamped loop to be placed on a bracket to secure an archwire thereto. The tool includes structure defining a path along which the chain is intended to be advanced in a forward direction toward the tips. A constriction zone formed in this path, adjacent its downstream end, functions to restrain successive chain loops at positions where successive end loops are placed for clamping between the tool tips. The chain is advanced along the path, in a loop-by-loop manner, by exerting a force on the chain in a downstream direction, to pull the restrained chain loop through the constriction zone by reversible loop elongation.

These and other objects and features of the present invention will become more fully apparent when the following detailed description of a preferred embodiment of the invention is read in connection with the accompanying drawings.

DESCRIPTION OF THE DRAWINGS

FIG. 3 is an enlarged, fragmentary view of the right end portion of the tool and chain in FIG. 1, illustrating use of the tool in fastening a clamped end loop in the chain on an orthodontic bracket.

FIG. 4 is a view like FIG. 3, illustrating the condition of the tool and chain as the chain is being advanced by one loop in the tool; and FIG. 5 is an enlarged sectional view taken generally along line 5—5 in FIG. 4.

DETAILED DESCRIPTION OF A PREFERRED EMBODIMENT OF THE INVENTION

Figure 1:
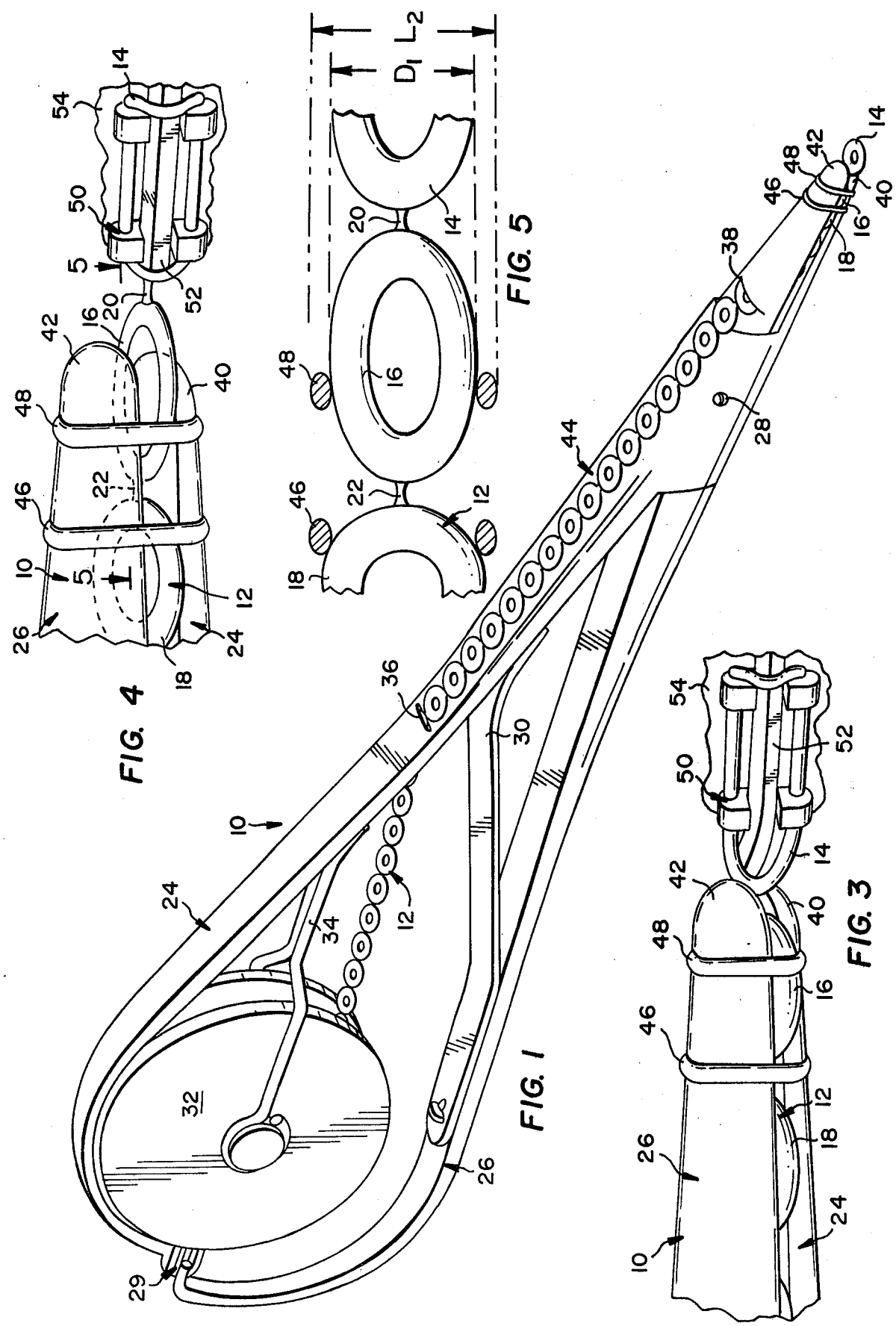
FIG. 1 is a perspective view of an applicator tool constructed according to the present invention for use in dispensing and clamping the loops in an elastomeric loop chain which is shown here in operative condition on the tool.

FIG. 1 shows an applicator tool 10 constructed according to the present invention, and an orthodontic loop chain 12 shown operatively in the tool. Chain 12 is composed of a series of elastomeric loops, such as loops 14, 16, 18, which are connected, to form a linear loop chain, by breakaway isthmuses, such as isthmus 20 connecting loops 14, 16, and isthmus 22 connecting loops 16, 18 (see FIGS. 4 and 5). The elastic deformability of the chain loops, and the strength of the isthmuses in the chain in transmitting forces exerted on the chain will be considered below, in the described operation of tool 10.

Viewing FIG. 1, tool 10 has a hemostat-like construction, including a pair of arms 24, 26 pivotally connected at 28. The tool can be locked in different operative conditions by a conventional ratchet-type lock 29 whose interacting serrated teeth components are formed at the handle ends of arms 24, 26. The lock is releasable, conventionally, by a squeeze and release action. A spring 30 mounted on arm 26, and constructed to make contact with arm 24 as the two arms are brought toward one another, functions to bias the two arms toward an open, unlocked condition.

A replaceable spool 32 on which chain 12 is wound is releasably mounted on arm 24 by a forked mounting member 34 for rotation about the spool's axis. Two slots 36, 38 formed in arm 24 receive chain 12 as shown. These slots are dimensioned to allow substantially unhindered movement of the chain loops therethrough.

Figure 2:
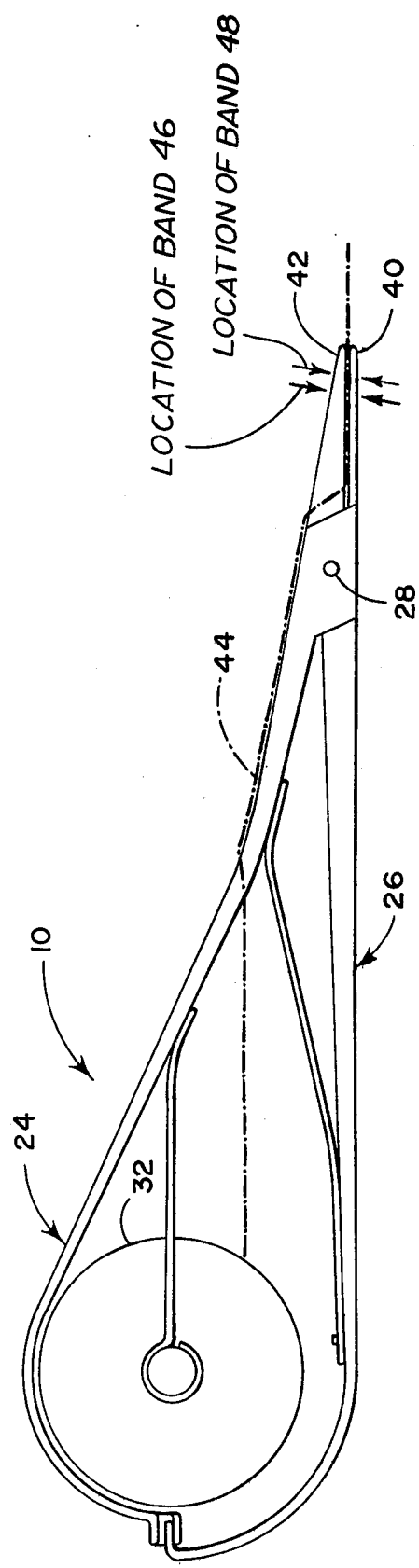
FIG. 2 (second plate of drawings) is a schematic side view of the tool and chain of FIG. 1, illustrating a travel path for the chain as the same is advanced to dispense successive loops.

The clamping end of tool 10 (the right end in FIG. 1) is further illustrated in FIGS. 3 and 4. The rounded clamping, or loop-gripping, tips associated with arms 24, 26 in the tool are indicated at 40, 42, respectively, in these figures. As can be seen clearly in FIG. 2, tool 10 includes structure defining a wandering path, indicated generally at 44, along which the chain moves in a downstream direction from spool 32 toward the loop-gripping tips in the tool.

Also included in tool 10 are two elastomeric band 46, 48 which encircle the tool's clamping tips at the positions shown. These bands, which may be conventional O-rings, are seated in suitable grooves formed in the two arm end regions. The two bands resist, but do not overcome, the biasing of spring 30 in maintaining the tool in a partially opened, unclamped condition when lock 29 is disengaged.

According to an important feature of the present invention, bands 46, 48 form a pair of axially spaced constrictions, which together function as a constriction zone through which successive loops in chain 12 must pass, by reversible loop elongation, as they are advanced toward the tool's clamping tips. With reference to FIG. 5, band 48 defines a constriction whose side-to-side dimension is indicated by $D_1$. The constriction formed by band 46 is slightly larger, owing to the taper in the clamping ends of arms 24, 26. The relaxed-state outer diameter of each loop in the chain is indicated at $L_2$ in this figure. In the particular embodiment of the invention being described herein, $D_1$ has a preferred value of about 0.09-inches, and $L_2$, of about 0.125-inches. Bands 46, 48 are also referred to herein as a restraining means.

The tool of the present invention is constructed for use with an orthodontic loop chain, such as chain 12, to facilitate ligating an orthodontic archwire to an orthodontic bracket, also referred to herein as a tooth appliance. Fragmentary portions of a conventional four-post bracket 50, and of an attached archwire 52, are seen in FIGS. 3 and 4. Bracket 50 is mounted conventionally on a band, shown fragmentarily at 54, which encircles a tooth, and which is attached thereto as by cementing.

In FIG. 3, the chain is shown in a condition in which the chain's end loop 14 is tightly clamped between the gripping tips in the tool. With the loop thus clamped, the orthodontist applies a tensil force to the loop sufficient to produce the loop elongation necessary for stretching the same over the bracket and archwire, as shown. After loop 14 is mounted on bracket 50, the tool is unlocked to release the end loop. Spring 30 in the tool functions to place the tool in an open, unclamped condition.

The orthodontist now pulls back on the tool, with a relatively gentle pulling force, to advance the chain in the tool in an indexed manner by one loop. FIGS. 4 and 5 illustrate the resilient deformation and stretching which occurs in an end portion of the chain during such advancement. Here it can be seen that as the chain is pulled in a downstream direction, by pulling the tool toward the left in the figures, loop 16, which was previously nested between bands 48, 46, is pulled through the constriction formed by band 48. Passage through this constriction is accommodated by elongation of the loop, resulting in the substantially eliptical loop shape seen in FIG. 5.

The downstream pulling force applied to the chain to advance loops 16, 18 through bands 48, 46, respectively, produces a resilient stretching in the associated downstream isthmuses in the chain. The kind of chain used herein with tool has isthmuses which are constructed to withstand, without breaking, a force somewhat greater than that required to advance the chain in the tool by one loop.

After the chain has been advanced by one loop, loop 16 is clamped by engaging lock 29. Isthmus 20 connecting loops 14, 16 is then broken by giving a sharp tug on the tool sufficient to stretch isthmus 20 beyond its breaking point. Loop 16 is now ready for fastening to another bracket.

Tool 10, in cooperation with an orthodontic loop chain of the type described, allows an orthodontist to clamp an orthodontic loop, attach that loop to a bracket, and place another loop in a clamped condition in the tool, in a simple series of one-hand steps. The invention thus saves time and effort in an orthodontic procedure.

The relative size and strength characteristics in tool 10 and chain 12 which have been set forth herein enable the kind of loop fastening practice just described. The dimensional relationship between the chain and tool can be scaled up or down in a proportionate manner to accommodate the handling of chains having different sizes of loops.

While a preferred embodiment of the invention has been described herein, it will be apparent to those skilled in the art that various changes and modifications may be made without departing from the spirit of the invention.

It is claimed and desired to secure by Letters Patent:

1. An applicator tool for use with an orthodontic loop chain to facilitate attaching, through the use of individual loops in the chain, an orthodontic archwire to orthodontic tooth appliances, where the chain is composed of a series of elastically deformable loops connected by breakaway isthmuses, said tool comprising
   a pair of pivotally connected arms,
   a pair of loop-gripping tips adapted for clamping an end loop in the chain in a manner permitting the end loop to be placed on a tooth appliance, to secure an archwire thereto,
   a chain dispenser mounted on one of the arms, adjacent the other end thereof,
   means defining a path along which the chain is intended to be advanced in a forward direction from said chain dispenser toward said tips, and
   means elastically encircling said tips forming a constriction zone in said path through which an end-adjacent loop in the chain is adapted to pass, by reversible loop elongation produced by the application of a downstream force on the chain which is substantially less than that required to break an isthmus in the chain.

2. The tool of claim 1, wherein said means forming said encircling means includes a pair of elastomeric bands encircling said tips.

* * * * *